US008388585B2

(12) United States Patent
Tomes et al.

(10) Patent No.: US 8,388,585 B2

(45) Date of Patent: Mar. 5, 2013

(54) DISPOSABLE URINE COLLECTOR WITH PAD AND SHELL

(76) Inventors: Kimberly L. Tomes, San Antonio, TX (US); Theresa Ernest, Fair Oaks Ranch, TX (US)

(*) Notice: Subject to any disclaimer, the term of this patent is extended or adjusted under 35 U.S.C. 154(b) by 1634 days.

(21) Appl. No.: 11/557,423

(22) Filed: Nov. 7, 2006

(65) Prior Publication Data

US 2008/0132861 A1 Jun. 5, 2008

(51) Int. Cl.
*A61F 5/44* (2006.01)

(52) U.S. Cl. ........................................ 604/329; 604/358

(58) Field of Classification Search .................. 604/367, 604/327–329, 385.01, 378, 385.13, 385.14, 604/385.3, 385.27, 385.25, 358; 4/144.1
See application file for complete search history.

(56) References Cited

U.S. PATENT DOCUMENTS

| | | | |
|---|---|---|---|
| 4,257,418 | A | 3/1981 | Hessner |
| 4,457,314 | A | 7/1984 | Knowles |
| 4,496,360 | A | 1/1985 | Joffe et al. |
| 4,578,073 | A | 3/1986 | Dysart et al. |
| 4,601,081 | A | 7/1986 | Sutton et al. |
| 4,608,046 | A | 8/1986 | Towfigh |
| 4,645,251 | A | 2/1987 | Jacobs |
| 4,701,177 | A | 10/1987 | Ellis et al. |
| 4,731,065 | A | 3/1988 | Yamada |
| 4,756,029 | A | 7/1988 | Zieve et al. |
| 4,781,713 | A | 11/1988 | Welch et al. |
| 4,857,064 | A | 8/1989 | Mendoza |
| 4,937,889 | A | 7/1990 | Strickland |
| 4,944,735 | A | 7/1990 | Mokry |
| 4,996,727 | A | 3/1991 | Wyatt |
| 5,301,806 | A | 4/1994 | Olson |
| 5,318,549 | A | 6/1994 | Yang |
| 5,354,132 | A | 10/1994 | Young et al. |
| 5,370,637 | A | 12/1994 | Brodeur |
| 5,404,999 | A | 4/1995 | Bednar |

(Continued)

FOREIGN PATENT DOCUMENTS

| | | |
|---|---|---|
| EP | 0 788 327 B1 | 7/2001 |
| WO | 96/10356 A1 | 4/1996 |

(Continued)

OTHER PUBLICATIONS

The Survival Center, "Disposable Emergency Toilet Supplies" http://www.survivalcenter.com/Emergency%20Toilet%20Supplies.html (printed Aug. 7, 2007).

(Continued)

*Primary Examiner* — Tatyana Zalukaeva
*Assistant Examiner* — Benedict L Hanrahan
(74) *Attorney, Agent, or Firm* — Cox Smith Matthews Incorporated

(57) ABSTRACT

A disposable urine collection device may include an absorbent pad disposed proximate to the inner surface of a shell. The device may be contoured to be positioned against and enclose the urinary area of a user such that the absorbent pad may absorb a quantity of urine associated with a complete urinary discharge from the user. The absorbent pad may be formed from one or more commercially available diapers. One or more elastic cuffs may be provided to conform to the user's urinary area and to help contain the flow of urine as it is discharged from the user. An invertible bag may be attached to the bottom of the shell so that the user may conveniently enclose the absorbent pad after use and dispose of the device in a sanitary manner.

17 Claims, 4 Drawing Sheets

U.S. PATENT DOCUMENTS

| | | | |
|---|---|---|---|
| 5,405,342 A | 4/1995 | Roessler et al. | |
| 5,417,680 A | 5/1995 | Kimura et al. | |
| 5,423,788 A * | 6/1995 | Rollins et al. | 604/385.21 |
| 5,438,708 A | 8/1995 | Jacovitz | |
| 5,473,789 A | 12/1995 | Oster | |
| 5,486,168 A | 1/1996 | Runeman et al. | |
| 5,558,659 A | 9/1996 | Sherrod et al. | |
| 5,613,959 A * | 3/1997 | Roessler et al. | 604/364 |
| 5,662,630 A | 9/1997 | Raynie | |
| 5,678,564 A | 10/1997 | Lawrence et al. | |
| 5,740,554 A | 4/1998 | Reed | |
| 5,752,946 A | 5/1998 | Boberg et al. | |
| 5,885,262 A | 3/1999 | Wheeler | |
| 5,885,265 A | 3/1999 | Osborn, III et al. | |
| 5,895,349 A | 4/1999 | Tihon | |
| 5,966,748 A | 10/1999 | Young et al. | |
| 5,991,932 A | 11/1999 | Wagner | |
| 6,025,535 A | 2/2000 | Octavio et al. | |
| 6,116,780 A | 9/2000 | Young et al. | |
| 6,183,454 B1 | 2/2001 | Levine et al. | |
| 6,186,990 B1 | 2/2001 | Chen et al. | |
| 6,202,224 B1 | 3/2001 | Freeman | |
| 6,222,091 B1 | 4/2001 | Beihoffer et al. | |
| 6,224,582 B1 * | 5/2001 | Zachery | 604/385.14 |
| 6,258,997 B1 | 7/2001 | Johansson et al. | |
| 6,324,704 B1 | 12/2001 | Imo | |
| 6,434,757 B1 | 8/2002 | Filsouf | |
| 6,468,256 B1 | 10/2002 | Mishima | |
| 6,514,602 B1 | 2/2003 | Zhao et al. | |
| 6,912,737 B2 | 7/2005 | Ernest et al. | |
| 7,171,699 B2 | 2/2007 | Ernest et al. | |
| 2004/0216220 A1 * | 11/2004 | Ernest et al. | 4/144.1 |
| 2007/0192948 A1 | 8/2007 | Ernest et al. | |

FOREIGN PATENT DOCUMENTS

| | | |
|---|---|---|
| WO | 2004/047676 A2 | 6/2004 |
| WO | 2004/047676 A3 | 6/2004 |
| WO | PCTUS0783626 | 6/2008 |

OTHER PUBLICATIONS

Safety Central, "Travel John Portable Pocket Toilet: Resealable Disposable Urinal Pouch" http://www.safetycentral.com/trdiurpo3pa.html (printed Aug. 7, 2007).

Spare Bladder, "Don't get caught up a tree without your . . . Spare Bladder" http://www.sparebladder.com/ (printed Aug. 7, 2007).

Alpha/Rubicon, "Women: No toilet? No problem!" by: Stella, Nov. 26, 2005 http://www.alpharubicon.com/med/womengottago.htm (printed Aug. 7, 2007).

Naval Safety Center, "To Pee or Not to Pee" by an anonymous female aviator, Mar. 2003 http://www.safetycenter.navy.mil/media/approach/issues/mar03/topeeornot.htm (printed Aug. 7, 2007).

Send2Press Newswire, "Hit P-mate Device Coming to the United States—Allowing Women Worldwide to Pee Standing Up!" Edited by Christopher Simmons, Oct. 17, 2005 http://www.send2press.com/newswire/print/news_2005-10-1017-008.shtml (printed Aug. 7, 2007).

Treehugger, "Peeing in your pants—the ideal public toilet accessory for women" by Petz Scholtus, Barcelona on Sep. 26, 2005 http://www.treehugger.com/files/2005/09/peeing_in_your.php (printed Aug. 7, 2007).

Magic Cone, "A Disposable urinal funnel for external use" http://www.magic-cone.com/ (printed Aug. 7, 2007).

P-Mate USA, "How to use" http://www.pmateusa.com/?site_id=224&id_sub=2283&page_id=2283 (printed Aug. 7, 2007).

Ace'S Pilot Shop, "Travel John Personal Urination Pouch" http://www.acespilotshop.com/pilot-supplies/safety/travel-john.htm (printed Aug. 7, 2007).

Aircraft Spruce & Specialty Co., "Portable Urinals—Lady J Adapter" http://www.aircraftspruce.com/catalog/pspages/liljohn2.php (printed Aug. 7, 2007).

* cited by examiner 76b
74
76a
72
82
80
30
70
20
10
80
82

DISPOSABLE URINE COLLECTOR WITH PAD AND SHELL

FIELD

This application relates generally to a urine collecting device, and more particularly to a self-contained disposable urine collecting device which allows for comfortable and hygienic urination.

BACKGROUND

A number of urinary devices exist which cater to infants and incontinent adults. These devices, such as diapers worn around the waist, catheters, and bedpans, all serve to direct the flow of urine away from the user when the user is incontinent. Much less common are urinary devices which cater to users who are continent but who nonetheless require a convenient and sanitary method of urine disposal. Such people often face a dilemma regarding the issue of where to urinate, especially while traveling in a car, airplane, or other vehicle. For example, individuals caught in traffic jams or snowstorms have limited options available for urination, and in remote areas public restrooms are often unavailable. Even when public restrooms are available, they are sometimes so filthy or unsafe that use of these facilities is undesirable. While some users may resort to outdoor urination, this option can be uncomfortable and socially stigmatizing. The problem is particularly troublesome for female aircraft pilots who frequently must endure several hours without the ability to urinate.

The alternative of delaying urination for extended periods of time while waiting to arrive at a suitable destination presents other undesirable problems. Apart from the obvious discomfort, the practice of delaying urination can result in medical problems for certain individuals who are at risk for bladder and kidney infections. Additionally, for certain individuals suffering from urinary urgency, loss of sphincter control, and various other conditions, delaying urination for extended periods of time may not be possible.

Another important use of a disposable urinary device catering to continent users is in medical settings, such as hospitals and nursing homes, where individuals are often unable or reluctant to make use of restroom facilities or to use a bedpan due to discomfort or weakness from surgery, illness, or other mobility constraints. It is preferable to avoid catheterization of such individuals whenever possible. Additionally, such individuals often decline to wear disposable diaper products around the waist due to chaffing, odor, and discomfort.

SUMMARY

A disposable urine collection device for use by a person may include an absorbent pad disposed proximate to the inner surface of a relatively stiff shell. The device may be contoured to be positioned against and enclose the urinary area of the user such that the absorbent pad may absorb and retain a quantity of excreted urine associated with a complete urinary void by the user. The absorbent pad may be formed from one or more commercially available diapers, which may comprise double-layered elastic cuffs. The ends of the absorbent pad and the outer layers of the elastic cuffs may be attached to the shell such that the inner layers of the elastic cuffs stand upright and help contain the flow of urine as it is discharged from the user. An invertible bag may be attached to the bottom of the shell so that the user may conveniently enclose the absorbent pad after use and dispose of the device in a sanitary manner.

DETAILED DESCRIPTION

As used herein, the following terms should be understood to have the indicated meanings:

When an item is introduced by "a" or "an," it should be understood to mean one or more of that item.

"Absorbent pad" means a mass of compressible material having a capacity for absorbing a quantity of liquid.

"Attached" means fastened or held in place in any manner, including but not limited to one or more stitches, staples, brads, rivets, nails, screws, glue, adhesive, welding, melting, fusing, tape, tension, compression, friction, or a combination thereof.

"Biodegradable" means capable of being broken down into substantially harmless products by the action of living things.

"Comprises" means includes but is not limited to.

"Comprising" means including but not limited to.

"Cuff" means a flexible barrier.

"Elastic" means having a capacity for stretching and a tendency to return to an initial state after deformation.

"Having" means including but not limited to.

"Hydrophilic" means having a substantial affinity for water or other liquids comprising water, including but not limited to urine.

"Hydrophobic" means lacking a substantial affinity for water or other liquids comprising water, including but not limited to urine.

"Shell" means a generally concave structure that tends to retain its shape over a substantial period of time. A shell may or may not be biodegradable.

"Trough" means an open conduit adaptable for channeling a liquid.

"Waterproof" means substantially impervious to water or other liquids comprising water, including but not limited to urine.

Figure 1:
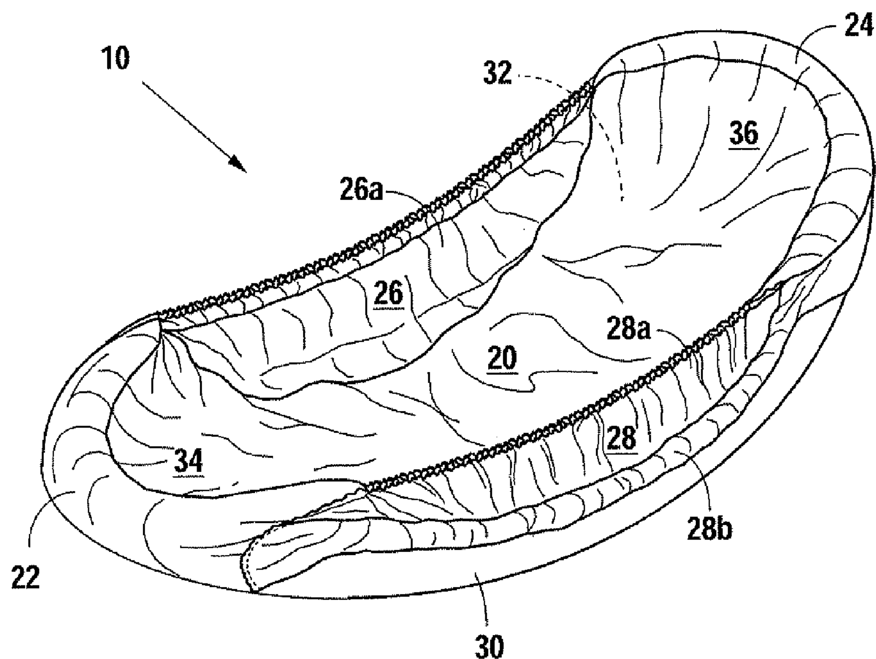
FIG. 1 is a perspective view of one embodiment of a disposable urine collection device.
Figure 2:
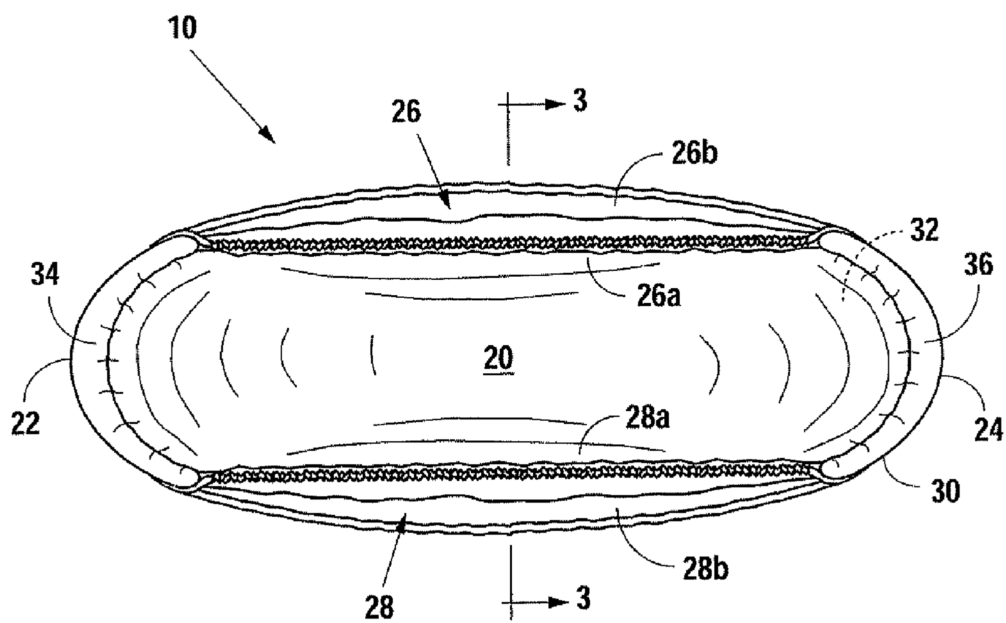
FIG. 2 is a top view of the urine collection device of FIG. 1.
Figure 3:
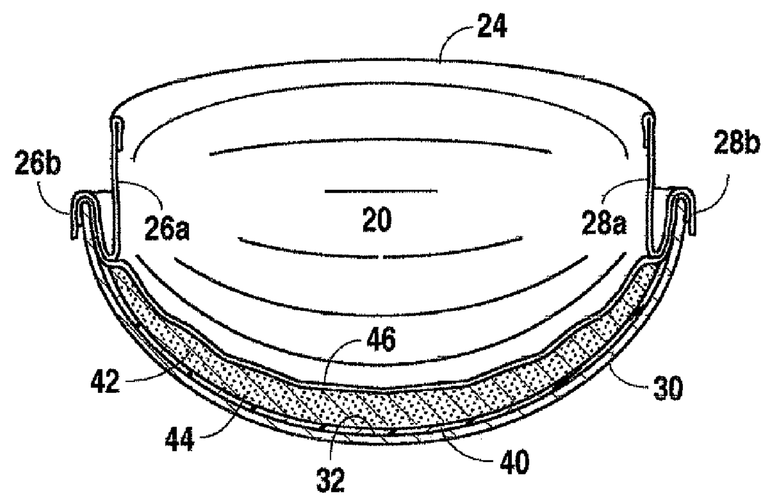
FIG. 3 is a sectional view of the urine collection device of FIG. 1 taken in the direction of arrows 3-3 as shown in FIG. 2.

Referring to FIGS. 1-3, a disposable urine collection device 10 may comprise an absorbent pad 20 attached to a relatively stiff shell 30. The shell 30 and absorbent pad 20 may be preformed, shaped, and sized such that the absorbent pad 20 generally conforms to the inner surface 32 of the shell 30. The absorbent pad 20 may have two double-layered elastic cuffs 26, 28, each of which has an inner layer 26_a_, 28_a_ and an outer layer 26_b_, 28_b_, respectively. Alternatively, the elastic cuffs 26, 28 may be attached to the shell 30 in addition to or in lieu of attachment to the absorbent pad 20. The absorbent pad 20 may be attached to the shell 30 by wrapping the ends 22, 24 of the absorbent pad 20 over the ends 34, 36 of the shell 30 such that the elastic cuffs 26, 28 are placed in tension in order to hold the absorbent pad 20 in place on shell 30. The absorbent pad 20 may also be attached to shell 30 with glue, adhesive, epoxy, stitching, staples, or any other suitable fastener, either in lieu of or in addition to the tension of elastic cuffs 26, 28. Similarly, the outer layer 26*b*, 28*b* of each double-layered cuff 26, 28 may be wrapped about and attached to the respective side edge of the shell 30. The attachment of the outer layers 26*b*, 28*b* to the shell 30 helps cause the respective inner layers 26*a*, 28*a* to stand substantially upright with respect to the shell 30, which creates a barrier to urine flow, yet the elastic nature of inner layers 26*a*, 28*a* allows the device 10 to conform comfortably to the user's body and effectively seal the device 10 about the user's urinary area during use to substantially prevent splattering of urine outside the device 10. Although one illustrated embodiment is shown having double-layered elastic cuffs 26, 28, the elastic cuffs may have only a single layer or more than two layers, and some embodiments may not have any elastic cuffs. The shell 30 may be constructed from molded paper pulp, biodegradable plastic, or another suitable biodegradable material, but the shell 30 may also be manufactured from any other desirable material that is relatively stiff and retains its shape either indefinitely or at least for a substantial period of time to allow use and disposal of urine collection device 10. The shell 30, which may be manufactured by molding, casting, or any other suitable method, provides a relatively stiff substrate which supports the absorbent pad 20 during use and which a user may readily grasp in order to urinate into the urine collection device 10 as described further below.

Referring more particularly to FIG. 3, the absorbent pad 20 may have multiple layers, one or more of which may be absorbent and one or more of which may be nonabsorbent. For example, a bottom layer 40, which engages the shell 30, may be a waterproof lining composed of materials such as nylon, polyester, polyethylene or polypropylene film, thermoplastic polymers, or other suitable materials to hold the urine within the absorbent pad 20 and prevent the urine from contacting the shell 30. Alternatively, the bottom layer 40 may not be waterproof and may allow the urine to contact shell 30, which may be desirable if the shell 30 is biodegradable, for example. The absorbent pad 20 may also comprise one or more intermediate layers 42 having one or more absorbent materials 44. In one embodiment, the absorbent material 44 may be a hydrophilic gel, which may comprise superabsorbent polymer particles containing water-absorbing resins, for example, but the absorbent material 44 may be any suitable material that has a capacity for absorbing or adsorbing urine, such as cloth, fabric, fibers, shavings, gauze, or combinations thereof. The absorbent pad 20 may also comprise a top layer 46 designed to allow urine to pass through layer 46 and into the absorbent pad 20 to be absorbed by the absorbent material 44. For example, layer 46 may comprise a hydrophobic material that allows urine to pass through it but maintains a relatively dry outer surface after wetting.

Figure 4:
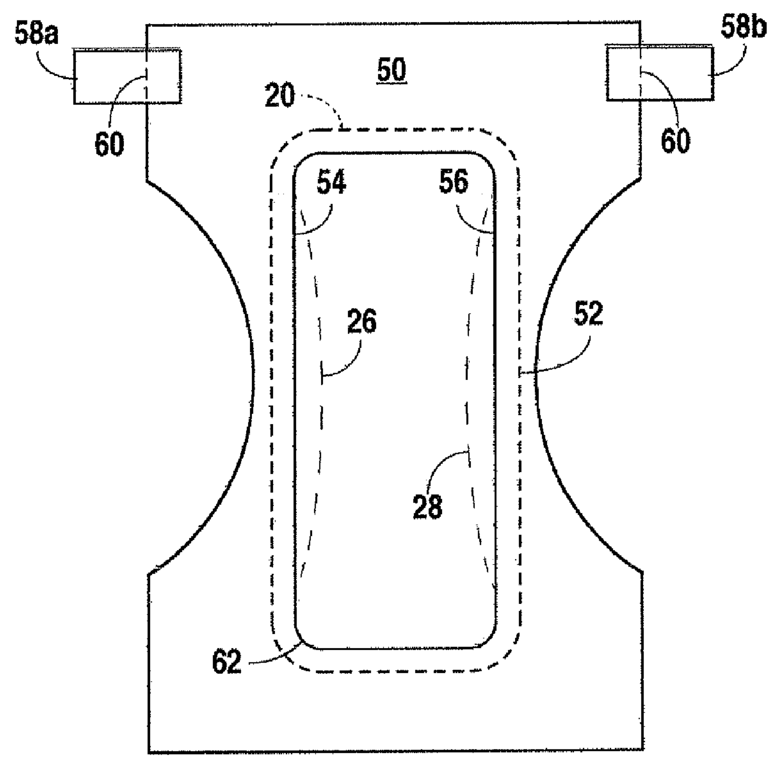
FIG. 4 is a plan view of a commercially available diaper that may be adapted for forming an absorbent pad for the urine collection device of FIG. 1.

Referring now to FIG. 4, in one embodiment of a urine collection device 10, the absorbent pad 20 may be formed from a commercially available diaper 50, such as a Huggies brand baby diaper, for example, which may have a pair of elastic leg cuffs 54, 56 and may or may not have a pair of tabs 58*a*, 58*b* comprising tape or hook and loop fasteners. In one embodiment, an unmodified diaper 50 may be used as an absorbent pad 20 for a urine collection device 10 as described above. In another embodiment, a suitable absorbent pad 20 may be formed from diaper 50 by simply cutting off the tabs 58*a*, 58*b*, which may be either discarded or used to fasten the absorbent pad 20 to the shell 30. The tabs 58*a*, 58*b* may be cut off along cut lines 60 or any other suitable cut lines. Alternatively, the diaper 50 may be cut along a suitable cut line, such as cut line 52, for example, to form the absorbent pad 20 of the urine collection device 10 as described above. In any of these embodiments formed from a diaper 50, the leg cuffs 54, 56 of the diaper 50 may conveniently serve as the elasticized cuffs 26, 28 of the absorbent pad 20 as described above. Additionally, the absorbent pad 20 may be cut along an edge 62, for example, so that additional absorbent materials may be inserted into the one or more intermediate layers 42 of the absorbent pad 20 to achieve a desired urine absorption capacity. For example, the absorptive capacity of the absorbent pad 20 may be increased by adding an additional amount of super absorbent polymer or other absorbent material. The ends of the absorbent pad 20 formed from diaper 50 may be slipped over and attached to the ends of the shell 30 as described above.

Figure 5:
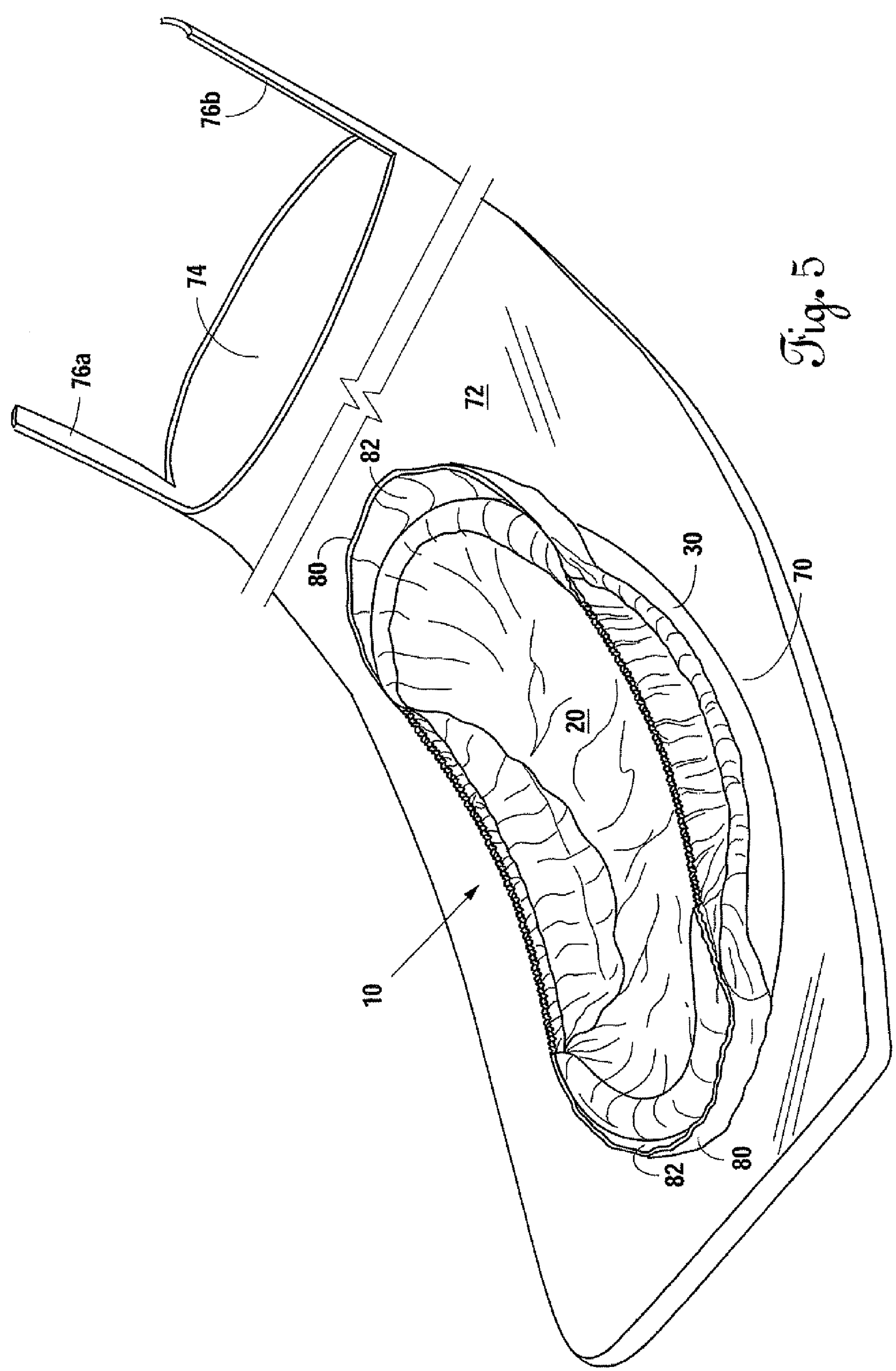
FIG. 5 is a perspective view of the urine collection device of FIG. 1 attached to an invertible bag.

As shown in FIG. 5, the bottom 70 of the shell 30 may be flattened such that the urine collection device 10 will remain stationary and upwardly-oriented when placed on a flat surface. Additionally, the urine collection device 10 may be attached to an invertible, flexible bag 72 for convenient and sanitary use and disposal. The flexible bag 72 may be large enough to permit complete inversion so as to completely enclose the urine collection device 10 after use. The flexible bag 72, which may be made from a waterproof material such as nylon, polyester, polyethylene or polypropylene film, thermoplastic polymers, plastic, fabric, or other suitable materials, may have an inner cavity 74 into which the user may insert a hand. The flexible bag 72 may comprise a glove for receiving a user's hand. The cavity 74 allows the user to grasp the bottom 70 of the device 10 through the flexible bag 72. Additionally, a suitable closure, such as tie flaps 76*a*, 76*b* or a twist tie, draw string, press seal, zipper, adhesive strip, or other suitable closure, for example, may be provided on the flexible bag 72 such that after the flexible bag 72 is inverted so as to enclose the urine collection device 10, the user may seal the flexible bag 72 around the urine collection device 10 for sanitary disposal. As shown in FIG. 5, the ends 80 of the absorbent pad 20 may be turned upward to form a trough 82 to help catch excess urine in the event of an overflow during an excessive discharge and redirect the overflow down toward the middle portion of the absorbent pad 20.

A urine collection device 10 as described above may be used by grasping the bottom 70 of the shell 30 with one hand and positioning the urine collection device 10 against the user's urinary area in such a manner that the user is able to direct the flow of urine onto the absorbent pad 20 so that the urine is absorbed by the absorbent material 44. The elastic cuffs 26, 28 of the absorbent pad 20 conform to the shape of the user's urinary area and help prevent splashing or splattering of urine outside the urine collection device 10. After voiding urine into the urine collection device 10, the user can remove the device 10 from the urinary area and dispose of it. If the urine collection device 10 is attached to a flexible bag 72 as described above, then the user may invert the bag 72 about the urine collection device 10 such that the bag 72 completely encloses the urine collection device 10, and the closure may then be closed to seal the used urine collection device 10 inside the bag 72. In some embodiments, the urine collection device 10 may be manufactured with a deodorizing substance contained within the absorbent pad 20 in order to reduce or eliminate odors. In a medical setting, if fluid intake and output measurement is important, the device 10 may be weighed before and after use to determine the quantity of urine excreted.

Figure 6:
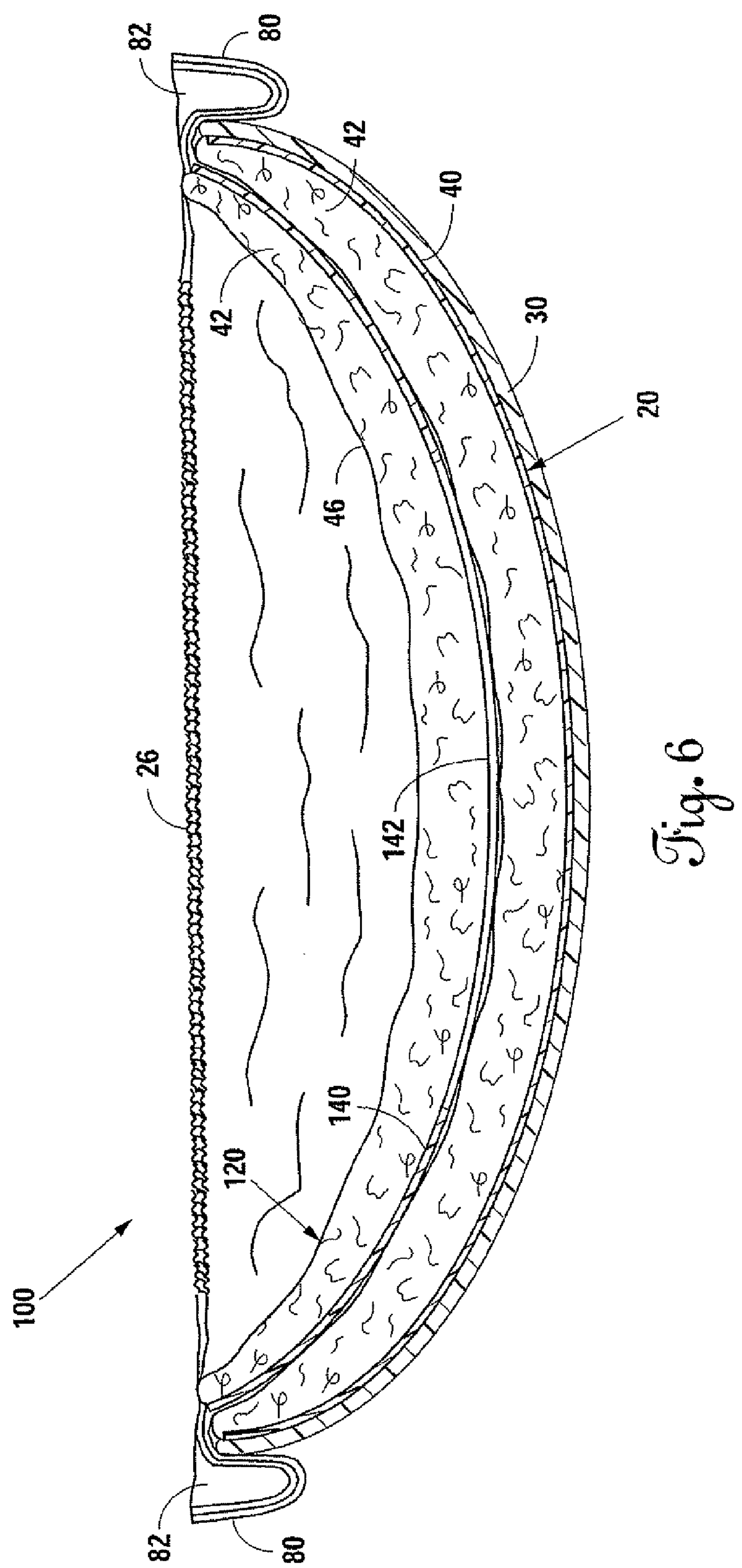
FIG. 6 is a sectional view of another embodiment of a disposable urine collection device.

Referring to FIG. 6, which is a longitudinal cross sectional view, an alternative embodiment of a urine collection device 100 is shown having an upper absorbent pad 120 overlying and in substantial juxtaposition to a lower absorbent pad 20, which is adjacent to a shell 30 as described above in connection with urine collection device 10. Absorbent pad 120 may be substantially the same as absorbent pad 20 as described above, except that absorbent pad 120 may have an opening 142 in its lower waterproof layer 140 to allow some urine to flow downward into lower absorbent pad 20 and be absorbed by absorbent materials in one or more intermediate layers 42 of pad 20. Of course, some urine may also be absorbed by absorbent materials in one or more intermediate layers 42 of pad 120. In this manner, the overall absorptive capacity of urine collection device 100 may be increased. As described above, if either or both of absorbent pads 20 and 120 are made from a commercially available diaper, either or both of absorbent pads 20 and 120 may be opened and additional absorbent materials, such as super absorbent polymers, may be inserted therein to increase the absorptive capacity to a desired level. In this embodiment, one or both ends 80 of each absorbent pad 20, 120 may be turned upward in a nested arrangement as shown to form a trough 82 to help catch excess urine in the event of an overflow during an excessive discharge and redirect the overflow down toward the middle portion of the absorbent pad 120, similar to the embodiment shown in FIG. 5.

A urine collection device 10 or 100 as described herein may be designed to accommodate persons of varying size, age, and gender. On average, human adult urinary discharges typically have a volume of about 240 mL to 300 mL, but adult urinary discharges may be as high as about 800 mL or more. An absorbent pad 20, 120 of a urine collection device 10, 100 as described herein may have any desired capacity for absorbing urine in order to absorb a complete urinary discharge from a user. For example, one embodiment may have a capacity for absorbing about 500 mL of urine in order to accommodate most adult urinary discharges. Another embodiment may have a capacity for absorbing about 1000 mL of urine in order to accommodate rather large adult urinary discharges. Alternatively, a urine collection device 10, 100 designed for children may have a reduced capacity for absorbing urine, such as, for example, about 100 mL to 200 mL. Persons of ordinary skill in the art will recognize that the foregoing urine absorption capacities are illustrative and not limiting.

Although the foregoing specific details describe certain embodiments of this invention, persons reasonably skilled in the art will recognize that various changes may be made in the details of this invention without departing from the spirit and scope of the invention as defined in the appended claims and considering the doctrine of equivalents. Therefore, it should be understood that this invention is not to be limited to the specific details shown and described herein.

What is claimed is:

1. A disposable urine collection device to be used by a person, said device comprising:

a shell having an inner surface;

an absorbent pad attached to said shell;

said absorbent pad having a shape adapted for generally conforming to said inner surface of said shell;

said absorbent pad having a capacity for absorbing a quantity of urine associated with a complete urinary discharge by the person; and at least one elastic cuff attached to at least one of said absorbent pad and said shell;

said at least one elastic cuff being adapted for generally conforming to the urinary area of the person;

said at least one elastic cuff being further adapted to substantially prevent splattering of urine outside said urine collection device as the person excretes urine into said urine collection device.

2. The disposable urine collection device of claim 1 wherein said absorbent pad and said at least one elastic cuff comprise at least a portion of a commercially available diaper.

3. The disposable urine collection device of claim 1 wherein said absorbent pad comprises:

a top protective layer;

a middle absorptive layer; and a bottom waterproof layer adjacent said shell.

4. The disposable urine collection device of claim 3 wherein said top protective layer comprises a hydrophobic material.

5. The disposable urine collection device of claim 3 wherein said middle absorptive layer comprises a hydrophilic material.

6. The disposable urine collection device of claim 5 wherein said hydrophilic material comprises a super absorbent polymer.

7. The disposable urine collection device of claim 1 further comprising a flexible bag attached to said shell, said bag being invertible so as to substantially enclose said shell and said absorbent pad.

8. The disposable urine collection device of claim 7 wherein said bag is waterproof.

9. The disposable urine collection device of claim 7 wherein said bag further comprises a closure.

10. The disposable urine collection device of claim 7 wherein said bag comprises a glove.

11. The disposable urine collection device of claim 1 wherein said shell comprises a biodegradable material.

12. The disposable urine collection device of claim 1 wherein said capacity for absorbing a quantity of urine is in the range of about 100 mL to about 1000 mL.

13. The disposable urine collection device of claim 1 wherein said capacity for absorbing a quantity of urine is about 500 mL.

14. The disposable urine collection device of claim 1 wherein said at least one elastic cuff comprises a double-layered elastic cuff having an inner layer and an outer layer, wherein said outer layer is wrapped about a side edge of said shell, and wherein said inner layer is disposed substantially upright with respect to said shell.

15. The disposable urine collection device of claim 1 wherein said at least one elastic cuff is placed in tension and helps keep said absorbent pad attached to said shell.

16. The disposable urine collection device of claim 1 wherein at least one end of said absorbent pad comprises a trough.

17. The disposable urine collection device of claim 1 wherein said absorbent pad comprises an upper absorbent pad in substantial juxtaposition to a lower absorbent pad, said upper absorbent pad comprising a bottom waterproof layer having an opening therein to allow urine to flow into said lower absorbent pad.

* * * * *